United States Patent [19]

Dyckman

[11] Patent Number: 5,435,971
[45] Date of Patent: Jul. 25, 1995

[54] STERILIZATION BIOLOGICAL TEST PACK
[75] Inventor: John Dyckman, Deer Park, N.Y.
[73] Assignee: Propper Manufacturing Co., Inc., Long Island City, N.Y.
[21] Appl. No.: 162,646
[22] Filed: Dec. 3, 1993

Related U.S. Application Data

[63] Continuation-in-part of Ser. No. 534,117, Jun. 6, 1990, abandoned.
[51] Int. Cl.⁶ ............................................. G01N 31/22
[52] U.S. Cl. ....................................... 422/61; 422/58; 435/291; 436/1
[58] Field of Search ..................... 422/58, 61; 436/1; 435/35, 291; 206/459, 807

[56] References Cited

U.S. PATENT DOCUMENTS

| | | |
|---|---|---|
| 4,579,715 | 4/1986 | Bruso . |
| 4,596,696 | 6/1986 | Scoville, Jr. . |
| 4,636,472 | 1/1987 | Bruso . |
| 4,828,797 | 5/1989 | Zwarun et al. . |
| 4,863,867 | 9/1989 | Joyce et al. . |
| 4,918,003 | 4/1990 | Macaro et al. . |

Primary Examiner—James C. Housel
Assistant Examiner—Jan M. Ludlow
Attorney, Agent, or Firm—Oppedahl & Larson

[57] ABSTRACT

A sterilization biological test pack includes a first plurality of apertured planar sheets of substantially porous paper disposed to form a stack. Each of the sheets defines a generally centrally disposed aperture, the apertures operatively defining together a single cavity extending through the stack. Second and third pluralities of unapertured planar sheets of substantially porous paper are disposed on opposed sides of the stack and aligned therewith to close the stack cavity at either end thereof and define a chamber about the cavity configured and dimensioned to receive a biological indicator. The first, second and third pluralities together define a sheet pad. A tray formed of unapertured gas-inhibiting material, has a base coextensive and aligned with the exposed side of the third plurality and four sidewalls transverse to the base together substantially covering the exposed edges of the pad. The tray and the pad together define an assembly. An organizer is disposed all about the periphery of the assembly to maintain the sheets and the tray in a predetermined spatial relationship while permitting the passage of steam and air to and from the assembly.

36 Claims, 5 Drawing Sheets

STERILIZATION BIOLOGICAL TEST PACK

CROSS-REFERENCE TO RELATED APPLICATION

This application is a continuation-in-part of application Ser. No. 534,117 filed Jun. 6, 1990 now abandoned.

BACKGROUND OF THE INVENTION

This invention relates generally to packs for testing the efficacy of a steam sterilization system. More specifically, the invention relates to a test pack which can be used with either a biological indicator or a chemical indicator to determine the efficacy of the sterilization system. The present invention is particularly, although not exclusively, useful for the testing of sterilizing equipment used for the sterilization of hospital and medical equipment.

The sterilization of medical equipment by exposure to steam is typically accomplished by using an autoclave. Normally, the equipment to be sterilized is placed within the autoclave and a vacuum may or may not be drawn depending on the particular procedure being followed. The sterilization medium, steam, is then introduced into the autoclave to permeate the equipment and sterilize it.

According to standard hospital procedures, steam sterilization equipment needs to be periodically tested to insure the sterilization process is efficacious. Such a test preferably requires subjecting spores of living microorganisms to the sterilization cycle and subsequently observing whether they have remained viable. To insure that the sterilization process is efficacious by sufficiently challenging the sterilization equipment, these spores need to be protected as well or better than they would ordinarily be protected if lodged in the most inaccessible recesses of the hospital packs to be sterilized.

Several procedures have been proposed to test the efficacy of steam sterilization equipment. Typical of these, and perhaps the best known and most widely used, is the procedure recently published by the Association for the Advancement of Medical Instrumentation (A.A.M.I.) as A.A.M.I. SSSA 1988 ("Good Hospital Practice: Steam Sterilization and Sterility Assurance"). According to the A.A.M.I. recommended practice, 16 freshly laundered all-cotton towels are folded by hospital personnel and stacked to construct a test pack into which a biological indicator is imbedded. This pack is then subjected to the sterilization cycle.

Although apparently efficacious for its intended purpose, the construction of a test pack according to the A.A.M.I. procedure is labor intensive and the resulting pack is relatively bulky. In light of these limitations, the present invention satisfies the need for a pre-assembled composite sterilization test pack which is convenient to handle and which will challenge steam sterilization equipment to the same degree as the 16 towel test pack. This is accomplished by surrounding a biological indicator with material which will delay steam entry to the indicator and provide the indicator with a degree of thermal insulation.

U.S. Pat. No. 4,636,472 discloses such a pre-assembled composite sterilization test pack which employs a combination of porous and non-porous materials in order to effect the desired interplay of steam entry to the indicator and degree of thermal insulation. The patented disposable sterilization test pack includes a base pad comprising a plurality of porous sheets having holes cut therethrough which are stacked to align the holes and form a cavity for receiving a sterilization indicator therein. A top pad and a bottom pad, each typically comprised of a plurality of gas permeable porous sheets, are respectively placed against the top and bottom surfaces of the base pad to confine the indicator within the cavity and help inhibit the flow of gas to and from the cavity. A gas impermeable layer is disposed against the top pad on its surface which is opposite from the base pad to further inhibit gas flow to and from the cavity by preventing the passage of gas into and out of the test pack wherever the impermeable layer is in contact with the porous material of the top pad.

When subjected to a sterilization cycle, the sterilization indicator (e.g., a biological or chemical indicator), positioned in the cavity of the test pack's base pad, will react according to the efficacy of the sterilization cycle. The entire stack of layers can be covered with a CSR (central supply room) overwrap material and held together with a tape having an indicator ink imprinted thereon to show when a pack has been subjected to a sterilization process.

The patented test pack has not proven to be entirely satisfactory in use. First, it was designed to simulate a proposed 14 towel test pack which was never adopted as an A.A.M.I. standard, and thus it is not suitable as a simulation of the more stringent 16 towel test pack. Second, the use of a gas impermeable layer substantially precludes gas flow to and from the cavity through a major surface (that is, the top) of the test pack and thereby emphasizes the flow of gas to and from the cavity along the edges and intermediate the pads (or intermediate the several sheets forming the pads) of the test pack. This is especially true in the preferred embodiments wherein there is also a gas impermeable layer disposed against the bottom pad. The resultant emphasis on gas flow along the edges of the test pack and intermediate the pads thereof makes the efficacy of the pack highly sensitive to the degree of tightness with which the overwrap material is applied thereto, by affecting the ability of the gas blocked by the gas impermeable layer to nonetheless reach the cavity by passage within the test pack intermediate the overwrap material and the sides of the stack and then intermediate the adjacent faces of the more permeable sheets of the stack.

Accordingly, it is an object of the present invention to provide a pre-assembled sterilization test pack which simulates the 16 towel test pack and tests the efficacy of steam sterilization biological equipment by challenging the accessibility of steam to the indicator and providing a requisite level of insulation for the indicator.

Another object provides such a test pack which can be easily altered to change sterilization indicators according to the needs and desires of the operator.

Still another object is to provide such a pre-assembled test pack which is small, compact, easily handled by hospital personnel, convenient to use, standardized, cost effective and easily manufactured.

It is also an object of the present invention to provide such a test pack which is not overly sensitive to the tightness of a wrapping or box about the stack.

It is a further object to provide such a test pack which uses a gas-inhibiting tray to inhibit the passage of gas into and out of one surface of the test pack and to control the passage of gas into and out of the edges of the test pack.

SUMMARY OF THE INVENTION

It has now been found that the above and related objects of the present invention are obtained in a sterilization biological test pack comprising first, second and third pluralities of sheets, a tray and an organizer. The first plurality is formed of apertured planar sheets of substantially porous material disposed to form a stack, each of the sheets defining a generally centrally disposed aperture, and the apertures of the sheets operatively defining together a single cavity extending through the stack. The second plurality is formed of unapertured planar sheets of substantially porous material disposed to one side of the stack and aligned therewith. The third plurality is formed of unapertured planar sheets of substantially porous material disposed to an opposed side of the stack and aligned therewith. The second and third pluralities of unapertured sheets extend across the stack cavity at either end thereof to close the same and define a chamber about the cavity configured and dimensioned to receive a biological indicator. The first, second and third pluralities together define a sheet pad. A tray formed of unapertured gas-inhibiting material has a base coextensive and aligned with the exposed side of the third plurality and four sidewalls transverse to the base together substantially covering the exposed edges of the pad. The tray and the pad together define an assembly. An organizer is disposed all about the periphery of the assembly to maintain the sheets and the tray in a predetermined stationary relationship while permitting the passage of steam and air to and from the assembly.

In a preferred embodiment, the sheets of the first, second and third pluralities are formed of paper and are of identical peripheral dimensions, typically 5×5 to 5×5.5 inch sheets. The chamber is about $1\frac{7}{8} \times \frac{1}{2}$ to $2\frac{5}{8} \times \frac{3}{4}$ inch in area. More particularly, the first, second and third, pluralities forming the assembly are either about 5×5 inch sheets, the chamber being $1\frac{7}{8} \times \frac{1}{2}$ inch in area, or about 5×5.5 inch sheets, the chamber being $2\frac{5}{8} \times \frac{3}{4}$ inch in area.

Preferably the tray is a gas-inhibiting plastic-laminated paperboard such as paperboard (e.g., solid bleached sulphate board) laminated on at least one side with plastic (e.g., polypropylene film). A preferred tray is solid bleached sulphate having a caliper of 0.020 fully laminated on one side by acrylic adhesive with a biaxially oriented polypropylene film 0.0014 inch thick. The base and each of the sidewalls of the tray are substantially planar.

In one preferred embodiment the organizer is an overwrap sheet of paper having a substantial porosity greater than that of the sheets of the pad. The first plurality is comprised of about 15-21 (preferably 18) sheets of paper having a basis weight of about 178 lbs., a caliper of about 0.02 in., and a Frazier porosity of about 1.2-2.0 cu.ft./sq. ft./min. per sheet, and the second and third pluralities are comprised of about 17-23 (preferably 20) and 4-8 (preferably 6) sheets, respectively, of paper having a basis weight of about 214 lbs., a caliper of about 0.02 in., and a Gurley porosity of about 12-35 sec. (using a 20 oz. cylinder). Thus the sheets of substantially porous paper for the second and third pluralities are of the same composition, and the sheets of substantially porous paper for the first plurality are of a different composition. The overwrap sheet is a conventional CSR wrap sheet and is disposed in a hospital pack format about the assembly.

In another preferred embodiment the organizer is a box having an integrally hinged flap on one end movable between an open position enabling passage thereinto and therefrom of the assembly and a closed position maintaining the elements of an assembly therein in a predetermined spatial disposition. The box with the flap in the closed position has an effective porosity greater than that of the sheet pad. The first, second and third pluralities are comprised of about 14-18 (preferably 16) 12-16 (preferably 14) and 4-8 (preferably 6) sheets, respectively, of paper having a basis weight of about 214 lbs., a caliper of about 0.02 in., and a Gurley porosity of about 12-35 sec. (using a 20 oz. cylinder). Thus, the sheets of substantially porous paper for the first, second and third pluralities are of the same composition. The box is preferably formed of solid bleached sulphate paperboard, and has pye locks at the corners thereof.

The present invention also encompasses the test pack and a biological indicator disposed in the chamber.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Referring now to the drawing, and in particular to FIGS. 1-4 thereof, therein illustrated is a sterilization biological test pack according to the present invention, generally designated by the reference numeral 10. As best seen in the exploded view of FIG. 1, the test pack 10 comprises a first plurality, generally designated 14, of apertured planar sheets 12 of substantially porous material disposed to form a stack.

Figure 1:
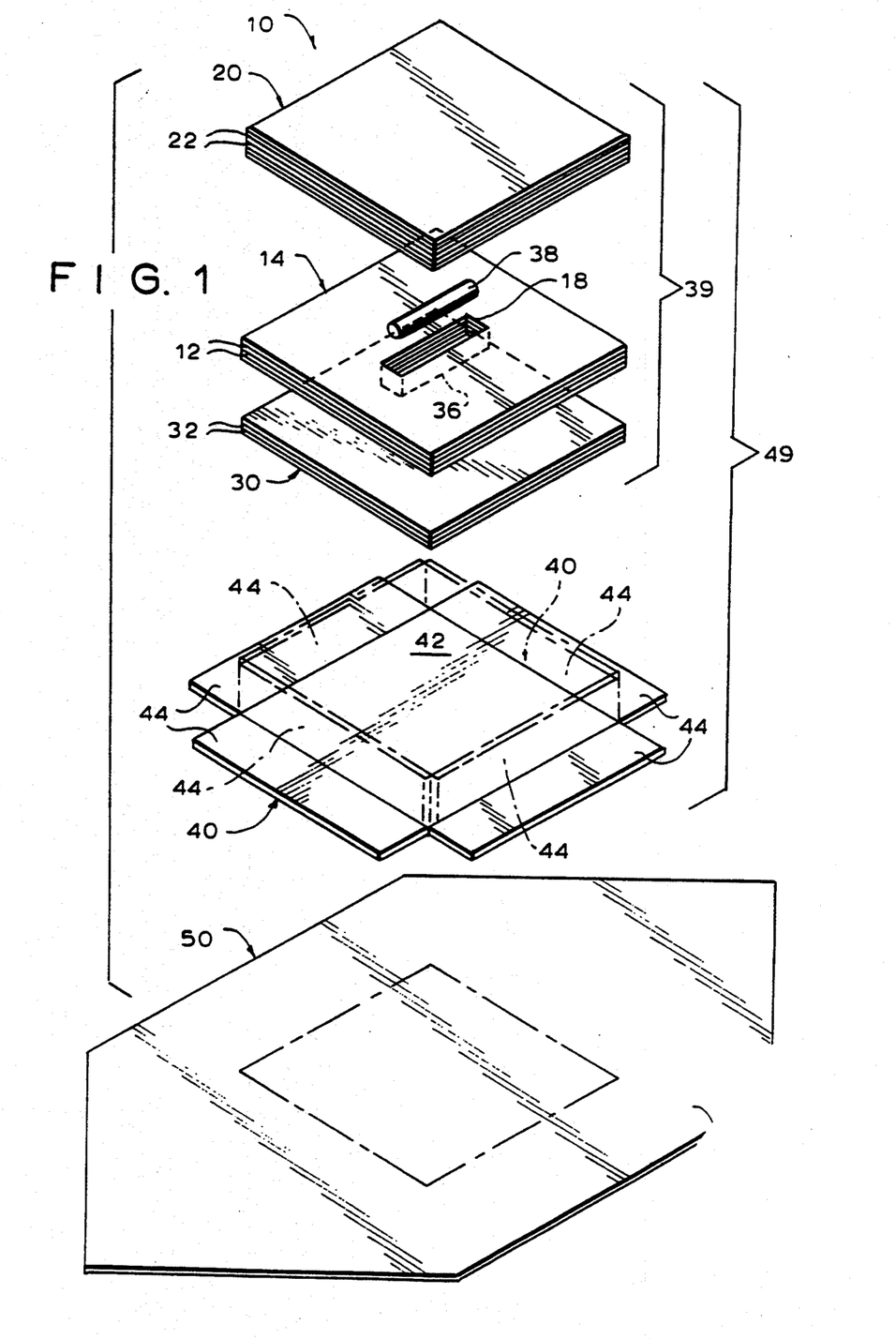
FIG. 1 is an exploded isometric view of a first embodiment of a test pack according to the present invention.

The sheets 12 are preferably formed of paper and are about 5×5 or 5×5.5 inch in area, although clearly smaller and larger sheets may be used. Each of the sheets 12 defines a generally centrally disposed aperture, the several apertures of the sheets 12 operatively defining together a single cavity 18 extending through the stack 14. The apertures are die cut, of rectangular configuration, about $1\frac{7}{8} \times \frac{1}{2}$ or $2\frac{5}{8} \times \frac{3}{4}$ inch in area (depending on the size of the biological indicator to be used), and vertically aligned, although clearly apertures of different configurations and dimensions are also useful. Preferably sheets of 5×5 in. paper with a $1\frac{7}{8} \times \frac{1}{2}$ in.

aperture or sheets of 5×5.5 in. paper with a 2⅝×¾ in. aperture are used. Depending upon the number of sheets 12 forming the stack 14, the height of the cavity 18 is about ⅜ in. for the 5×5 stack and about ½ in. for the 5×5.5 stack.

A second plurality generally designated 20 formed of unapertured planar sheets 22 of substantially porous material is disposed to one side of the stack 14 (for example, the top thereof) and aligned therewith. A third plurality generally designated 30 of unapertured planar sheets 32 of substantially porous material is disposed to an opposed side of the stack 14 (for example, the bottom thereof) and aligned therewith. The sheets 22, 32 are preferably formed of paper and are the same in peripheral dimensions as the sheets 12 used in the first plurality or stack 14.

Figure 3:
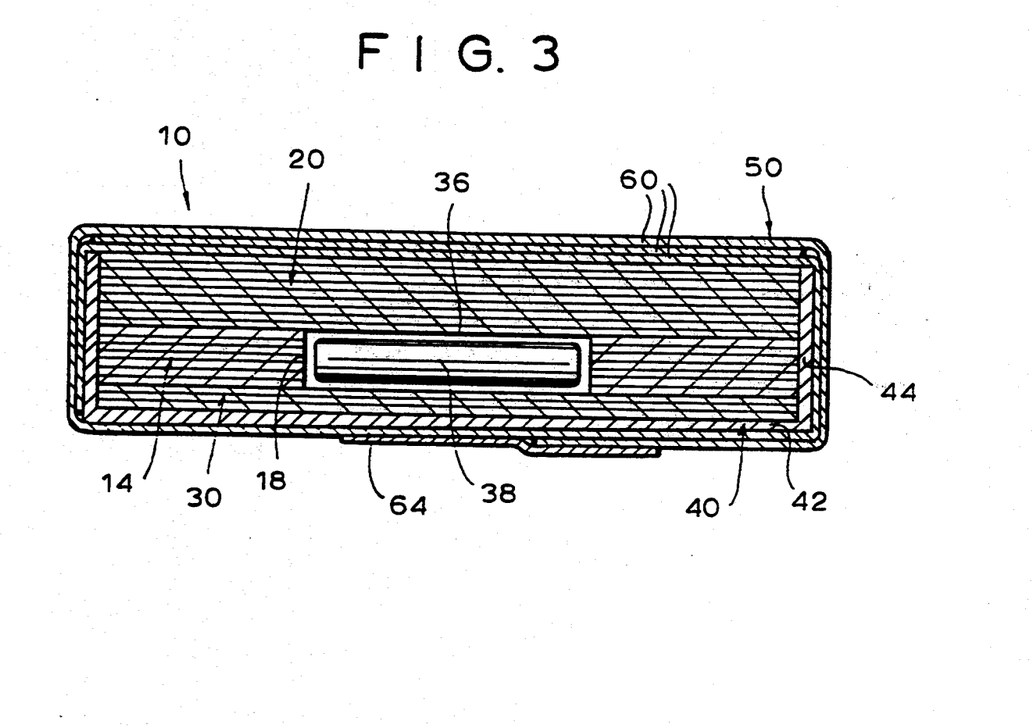
FIG. 3 is a sectional view thereof taken along the line 3—3 of FIG. 2.
Figure 4:
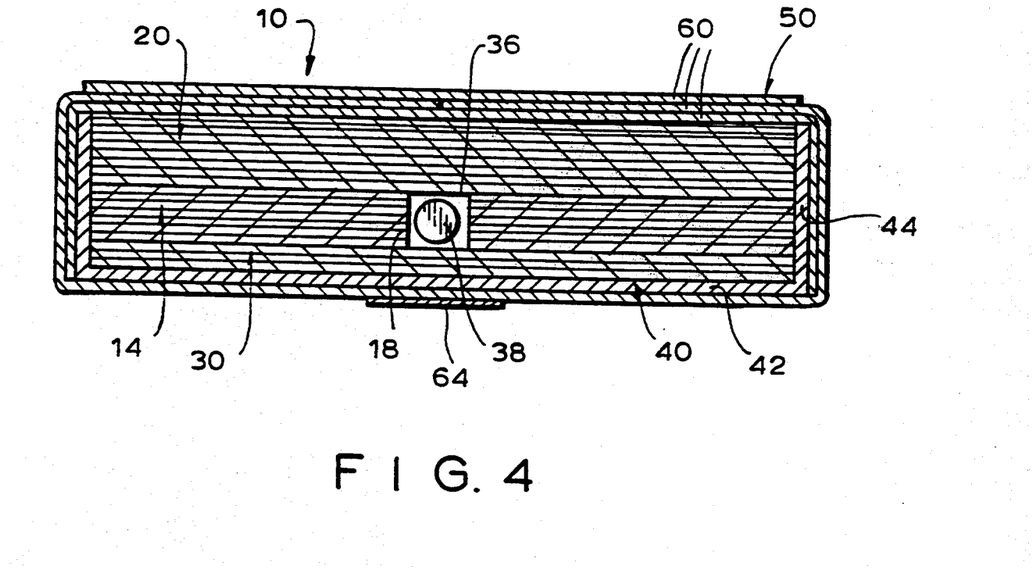
FIG. 4 is a sectional view thereof taken along the line 4—4 of FIG. 2.
Figure 5:
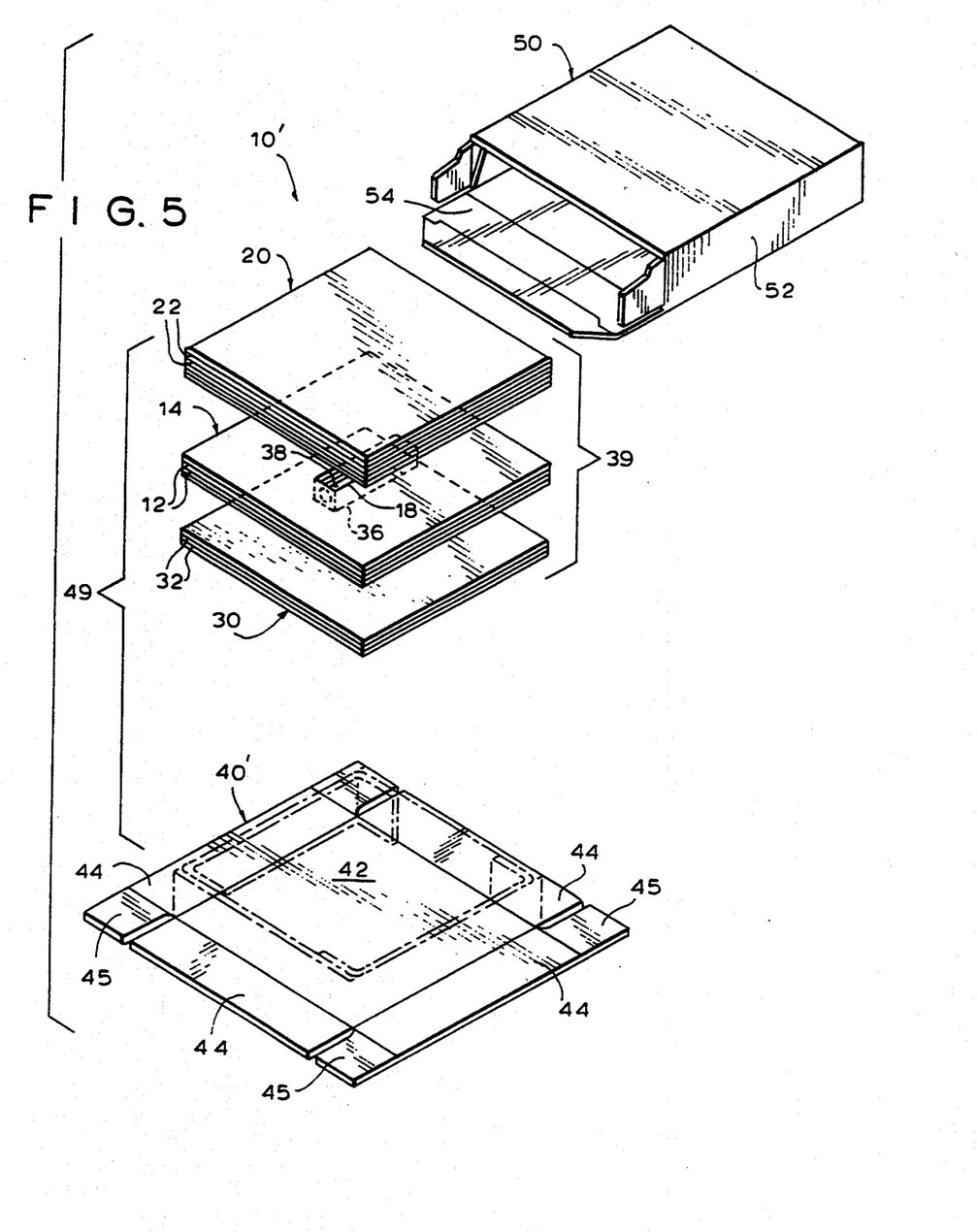
FIG. 5 is an exploded isometric view of a second embodiment of a test pack according to the present invention.
Figure 6:
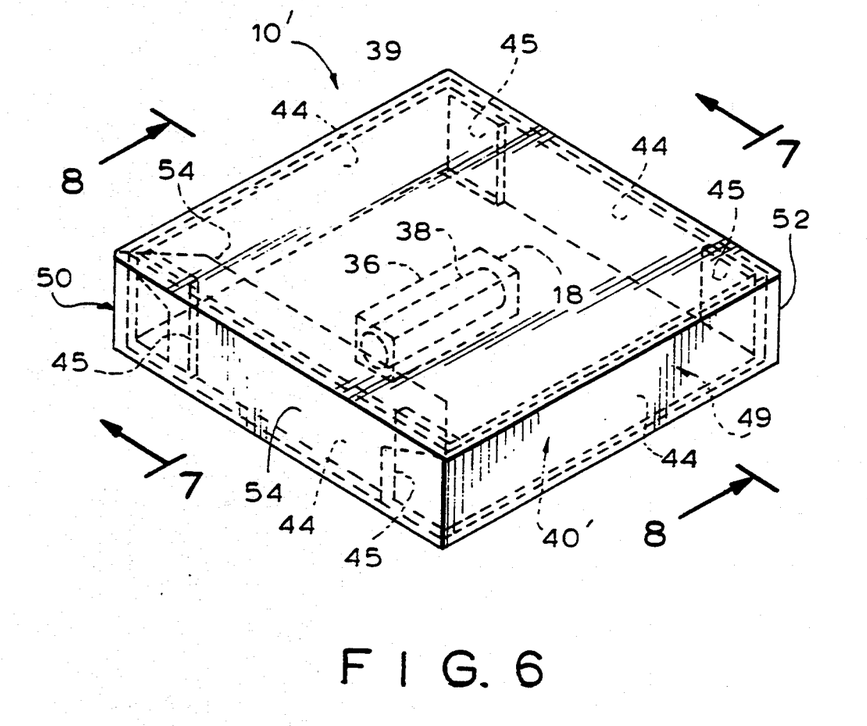
FIG. 6 is an isometric assembly view thereof.
Figure 7:
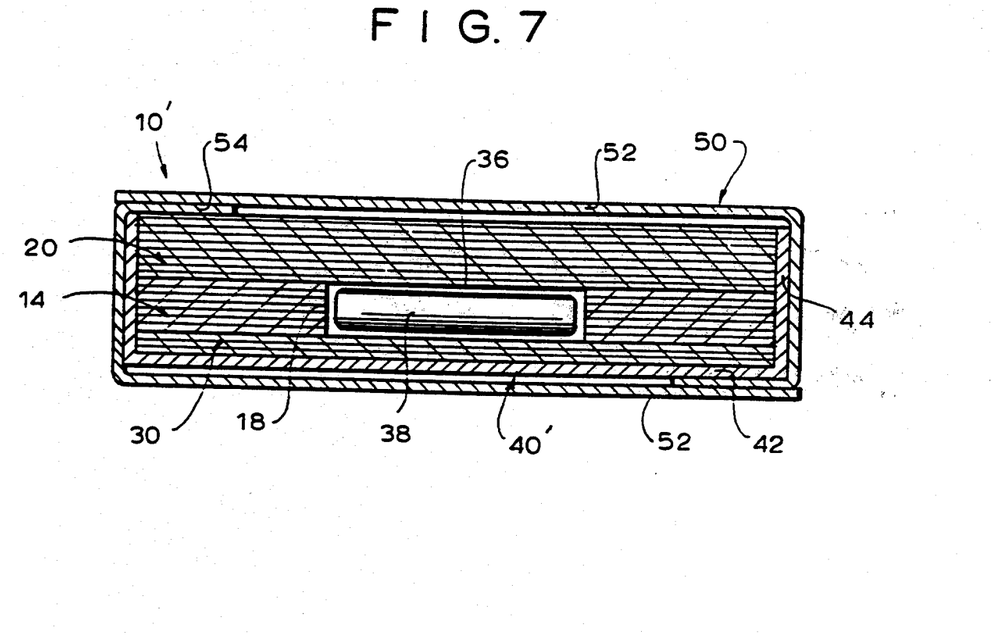
FIG. 7 is a sectional view thereof taken along the line 7—7 of FIG. 6.
Figure 8:
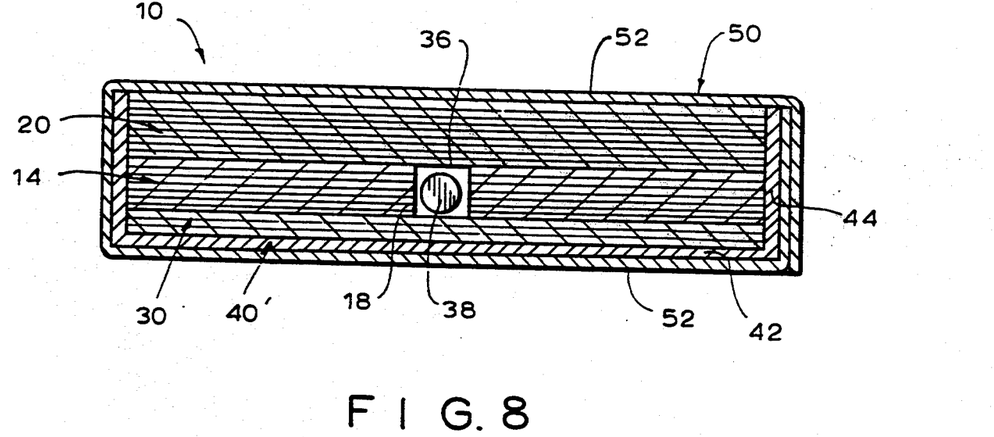
FIG. 8 is a sectional view thereof taken along the line 8—8 of FIG. 6.

The second and third pluralities 20, 30 of unapertured sheets 22, 32 extend across the stack cavity 18 at either end thereof (that is, at the top thereof and the bottom thereof) to close the cavity and define a chamber 36 (see FIG. 3) about the cavity 18 configured and dimensioned to receive a biological indicator 38 (see FIGS. 3 and 4). As one and two component biological indicators of the type suitable for use in the sterilization biological test pack 10 are well known in the art, a further specification thereof is not deemed necessary herein. The biological indicator is, of course, configured and dimensioned to be received within the chamber 36.

The first, second and third pluralities 14, 20, 30 together define a pad generally designated 39. Optionally one or more of these pluralities, or portions thereof, may be formed of substantially porous materials other than paper—e.g., foam.

A tray, generally designated 40, is comprised of a base 42 having dimensions similar to the sheets of the pad 39 in cross-section and four sidewalls 44 transverse to the base. Preferably, the tray base 42 and each of the tray sidewalls 44 are substantially planar (except for any tabs connecting one tray sidewall 44 with another). The base 42 is coextensive and aligned with the exposed side of the third plurality 30—that is, the bottom of pad 39—and the sidewalls 44 extend upwardly to about the top of the second plurality 20—that is, extend transverse to the base for a length substantially equal to the combined height of the first, second and third pluralities 14, 20, 30 of sheets when the pad 39 has the desired degree of compression for use in the sterilization biological test pack 10. If the tray sidewalls 44 extend substantially further upwardly than the top of the pad 39, then pad 39 cannot be sufficiently compressed in the test pack 10; if the tray sidewalls 44 do not extend upwardly substantially to at least the top of the pad 39, then the sheets of the pad 39 are overly sensitive to the degree of tightness with which they are held by the remainder of the test pack 10, as described below.

The tray 40 is formed of a gas-inhibiting plastic-laminated paperboard. The paperboard is laminated on at least one side with a gas-inhibiting material, such as plastic, and optionally on both sides. The paperboard is preferably a solid bleached sulphate board having a caliper of about 0.020 inches which is fully laminated on at least one side with the plastic. Any gas-inhibiting material, such as plastic, may be used, although polypropylene film, and especially a biaxially oriented polypropylene film, is preferred. The material may be laminated to the paperboard by any conventional means, such as an acrylic adhesive, capable of withstanding the anticipated moisture and temperature conditions to be experienced by a test pack. The tray base 42 inhibits the passage of gas into the pad 39 assembly through its bottom surface and the tray sidewalls 44 control the passage of gas through the edges of the pad 39. While the tray base 42 lies flat against the bottom of the pad 39 and therefore effectively inhibits the passage of gas through the pad bottom, the tray sidewalls 44 do not abut the pad edges as tightly and thus permit some controlled flow of gas through the pad edges.

In the first variation 40 of the tray shown in FIGS. 1-4, the four tray sidewalls 44 are connected only by the tray base 42 and thus the nonoverlapping sidewalls 44 may be folded upwardly about the pad edges after the pad is placed upon the tray base 42. Where it is desired to more fully restrict the flow of gas through the pad edges, the second variation 40′ of the tray shown in FIGS. 5-8 may be used. In the second variation 40′ an opposed pair of the tray sidewalls 44 also define side tabs 45 at each end thereof, the side tab or tabs 45 of one tray sidewall 44 of the opposed pair overlapping (but preferably not being secured to) the inner or outer surface of a tray sidewall 44 intermediate the pair. In this second variation 40′ of the tray, sufficient clearance must be provided between the tray sidewalls 44 (and tabs 45) and the pad 39 to enable the pad 39 to be dropped onto the tray base 42 past the tray sidewalls 44 (and tabs 45). While the operatively uninterrupted sidewall of the second variation 40′ (in turn formed by the individual planar sidewalls 44 and tabs 45) provides a more effective barrier to the passage of gas therethrough than the interrupted sidewalls 44 of the first variation 40, the requisite spacing between the inner surface of the tray sidewall 44 and the outer edge of the pad 39 provides a pathway for gas entering from above to reach the pad edges. Depending upon the variables employed (such as the spacing between the tray sidewall and pad edge in the second variation 40′), either variation may be preferred to the other for a given application.

The tray 40 or 40′ and the pad 39 together define an assembly 49.

An organizer, generally designated 50, is disposed all about the periphery of the assembly 49 to maintain the sheets 12, 22, 32 of pad 39 and the tray 40, 40′ in a predetermined spatial relationship while permitting the passage of gas (e.g. steam and air) to and from the assembly 49 and in particular the pad 39 thereof. Two different embodiments of organizers are preferred.

Figure 2:
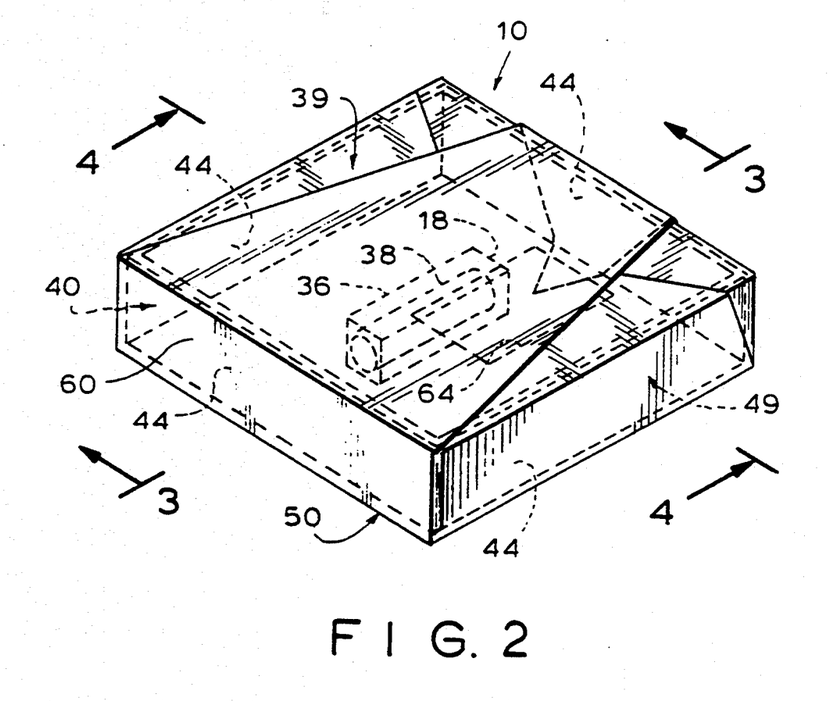
FIG. 2 is an isometric assembly view thereof.

In the first or overwrap embodiment 10, the organizer 50 is a single sheet 60 of unapertured gas-permeable material (commonly known as "C.S.R." or "sterilization wrap") disposed as an overwrap all about the periphery of the assembly. The highly porous overwrap sheet 60 has essentially no effect on the passage of steam and air into and from the assembly 49. The overwrap sheet 60 is preferably a conventional non-woven creped paper-like sterilization wrap. The overwrap sheet 60 is available under the trade name Dextex I from Dexter Corp. or under the tradename Steri-Wrap I from Propper Manufacturing Co., Inc. The overwrap sheet 60 is preferably configured as an elongated hexagon (maximum length 21 in. and maximum width 13 in. for a 5×5.5 assembly) and disposed in a conventional hospital wrap format about the assembly 49. The overwrap sheet 60 is fully and tightly wrapped around the assembly 49 so that the passage of steam and air into and from the assembly 49 is essentially directly through the overwrap sheet 60 rather than through fold openings or the like in the wrapping of the overwrap sheet 60. A short strip of standard one inch wide adhesive autoclave tape 64 holds the overwrap sheet 60 in the desired overwrapping orientation.

Referring now to FIGS. 5–8, in the second or box embodiment 10', the organizer 50 is a box 52 having on at least one end thereof an integrally hinged flap 54 (i.e., a flap connected to one box side by a foldline). The flap 54 is movable relative to the remainder of the box 52 between an open position enabling passage of the assembly 49 thereinto and therefrom and a closed position maintaining the elements of the assembly 49 therein in a predetermined spatial relationship. The box 52 with the flap 54 in the closed position has an effective gas-permeability greater than that of the pad 39. The box may be formed conveniently of solid bleached sulphate paperboard, such as 0.02 inch caliper paperboard. Preferably, but not necessarily, the box is provided with pye locks (as illustrated) at the corners thereof to prevent unintended opening thereof.

The overwrap embodiment 10 of the test pack of the present invention is, because of the tray sidewalls 44, less sensitive to the tightness with which the overwrap sheet 60 is applied to the assembly 49 than conventional overwrapped test packs and thus provides more reliable results regardless of who does the overwrapping or how tightly it is done on a given test pack. The box embodiment 10' of the test pack of the present invention is, because of the tray sidewalls 44, also less sensitive to minor variations in the dimensions of the box into which the assembly 49 is inserted than conventional box test packs and thus provides more reliable results. The organizer 50, whether it be the box 52 or the overwrap sheet 60, has an effective porosity which is at least equal to or greater than that of the pad 39 as a whole. The effective porosity reflects the porosity under the conditions of use—e.g., with the organizer 50 in the presence of steam under pressure. The effective porosity, of course, also takes into account not only the actual porosity (that is, the ability of the gas to pass directly through the material of the box or overwrap), but also the ability of the gas to pass about the organizer into the pad (for example, between the overlaps of the wrapped overwrap sheet 60 and between the end flaps 54 and the remainder of the box 52 in the box embodiment).

In the box embodiment 10' of the present invention, the first, second and third pluralities 14, 20, 30 are optimally comprised of about 14–18 (preferably about 16), 12–16 (preferably 14) and 4–8 (preferably 6) sheets of heavy porous paper. Thus, for the box embodiment 10', the sheets of substantially porous paper for the pad 39 are preferably of the same composition. By way of contrast, in the overwrap embodiment 10, the first, second and third pluralities 14, 20, 30 are optimally comprised of about 15–21 (preferably about 18), 17–23 (preferably 20) and 4–8 (preferably 6) sheets, respectively, of substantially porous paper. The first plurality 12 is comprised of a light substantially porous paper, while the second and third pluralities 20, 30 are each comprised of heavy substantially porous sheets, such as that used in connection with the box embodiment 10'. Thus, in the overwrap embodiment 10, while the sheets of the second and third pluralities 20, 30 are of the same composition, the sheets of first plurality 14 are of a different composition.

Each heavy porous paper sheet preferably has an appropriate basis weight of about 214 lbs. (per 3,000 square feet), an appropriate thickness of approximately 0.02 inch per sheet, and a Gurley porosity of approximately 12–35 sec. (using a 20 oz. cylinder); and each light porous paper sheet preferably has an appropriate basis weight of 178 lbs. (per 3,000 sq. ft.), an approximate thickness of approximately 0.02 inch per sheet, and a Frazier porosity of approximately 1.2–2.0 cu. ft./sq. ft./min. per sheet. Suitable paper is available from James River Corporation in Richmond, Va. However, clearly other substantially porous papers may be used for the porous sheets 12, 22, 32.

Frazier porosity is the measure of air permeability of sheet material as measured by the Frazier Differential Pressure Air Permeability Measuring Machine manufactured by Frazier Precision Instrument Company, Inc. of 210 Oakmont Avenue, Gaithersburg, Md. 02760. These measures of porosity are based on the differential pressure principle as measured by manometers. The porosity measure is given in cubic feet of air per square foot per minute at 0.5 inches of water pressure. Obviously, the Frazier porosities given herein in cubic feet per square foot per minute could be expressed by other standards of measurement. The porosity of stacked porous materials of the type herein used is substantially linear so that, if an individual sheet of material has a Frazier porosity of 90 cu. ft./sq. ft./min., a stack of ten sheets of such material will have a porosity 1/10 of that of the individual sheet or 9 cu. ft./sq. ft./min.

Another common measure of porosity of sheet material is the Gurley method which provides a measure of the time required for 100 ml. of air to pass through a one square inch area of the specimen material at a given pressure. The Gurley results are comparable to those of ASTM D726-58 (method A).

As will be apparent from the data above, the porosites and permeabilities specified for the various elements of the test pack of the present invention are specified for the elements at room temperature under standard Gurley and Frazier test conditions. It is believed in accordance with known principles that the paper elements of the present invention (that is, sheets 12, 22, 32 and the organizer 50) remain relatively constant in porosity over the ranges of temperature and pressure differentials encountered by the test pack during use. On the other hand, in accordance with well known principles, the plastic elements utilized in the tray 40 exhibit substantial increases in permeability at the elevated temperatures reached during the use cycle. Nonetheless, the tray 40, while exhibiting relatively less permeability at room temperature and a substantially higher permeability at the elevated temperatures, is effective to inhibit the passage of air and steam during the cycle. This is what is meant by reference to the tray as gas inhibiting.

It will be appreciated that only representative sheets 12, 22, 32 of each plurality 14, 20, 30 are illustrated in the drawing. It will further be appreciated that an overwrap embodiment may be used with sheets 12, 22, 32 of the same composition just as a box embodiment may be used with sheets 12, 22, 32 where the sheets 12 are of a different composition than the sheets 22, 32.

In use, the assembly 49 is built serially from the bottom to the top with a biological indicator 38 being placed within the cavity 18 of the stack 14 prior to closure of the chamber 36. The assembly 49 (now including the biological indicator 38) is either wrapped with overwrap sheet 60 as desired (with adhesive tape 64 finally applied in order to hold the overwrap sheet 60 in place) or inserted into a box 52 past open box flap 54

(and the open box flap 54 then closed). Alternatively, the test pack may be sold pre-assembled with a biological indicator 38 in the chamber 36.

The test pack of the present invention is uniquely customizable in that the basic sheet elements of the pack may be rearranged (i.e., relocated)—either by the test pack manufacturer or the ultimate test pack user—so as to modify the challenge presented by the test pack. Thus, the test pack of the present invention may be adapted for uses which require a more stringent protocol than the standard test, as well as for uses which require a more lenient protocol than the standard test. As long as the same number of sheets are used to form a pad 39, the pad 39 is combinable with a tray 40, 40' to form an assembly 49 which can be employed with an organizer 50, regardless of whether the organizer 50 is a overwrap 60 or box 52. In the case of the overwrap 60, the tray sidewalls 44 will still ensure an appropriate tightness of the overwrap about the assembly 49, and, in the case of the box 52, the assembly 49 will still fit therewithin.

Thus, as one or more of the sheets 22 of the second plurality 20 are removed therefrom and added to the sheets 32 of the third plurality 30, the biological indicator 38 in the chamber 36 of the stack cavity 18 of the first plurality 12 will move upwardly in the pad 39 and assembly 49, thus increasing exposure of the biological indicator 38 to the steam. This occurs because the porous sheets 22 of the diminished second plurality 20 constitute less of an impediment to the passage of steam than the tray base 42. The greater the number of sheets 22 relocated into pad 30, the less the challenge of the thus diminished second plurality 20. On the other hand, as one or more of the sheets 32 of the third plurality 30 are removed therefrom and added to the sheets 22 of the second plurality 20, the biological indicator 38 in the chamber 36 of the stack cavity 18 of the first plurality 12) will move downwardly, further from the top of the pad 39 or assembly 49 and closer to the tray base 42. The greater the number of sheets 32 relocated to the thus enlarged second plurality 20, the thinner the third plurality 30 and the greater the challenge provided as the biological indicator 38 is closer to the less permeable tray base Accordingly, one can easily customize the test pack of the present invention from the standard construction to a customized construction simply by relocating porous sheets 22, 32 as necessary to modify in the desired direction the spacing between the biological indicator 38 and the tray base 42. Accordingly, the test pack of the present invention is customizable either by the manufacturer, or, when it is provided with a removable organizer (whether an overwrap or a box) as shown in order to enable access to the pad 39, by the user. The customization is made possible by the second and third pluralities 20, 30 being codependently variable by the user (i.e., one or more of the sheets being removed from one plurality and added to the other plurality) so long as the total of the second and third pluralities 20, 30 remains a constant (i.e., so that the combined number of sheets in the second and third pluralities, and thus the combined height thereof, is unchanged).

To summarize, the present invention provides a test pack which simulates a 16 towel test pack and is small, compact, easily handled by hospital personnel, convenient to use, standardized, cost effective and easily manufactured. It is easily altered to change sterilization indicators as desired. The test pack is not overly sensitive to the tightness of a wrapping or box about the pad and employs a gas-inhibiting tray to inhibit the passage of gas into and out of the bottom of the test pack and to control the passage of gas into and out of the edges of the test pack Now that the preferred embodiments of the present invention have been shown and described in detail, various modifications and improvements thereon will become readily apparent to those skilled in the art. Accordingly, the appended claims are to be construed broadly and in a manner consistent with the spirit and scope of the invention described herein.

What is claimed is:

1. A sterilization biological test pack for holding a biological indicator, the pack being suitable for use on its base in a gravity displacement steam sterilizer, comprising:

(A) a first plurality of apertured planar sheets of substantially porous material disposed to form a stack, each of said sheets defining only a generally centrally disposed aperture, and said apertures of said sheets operatively defining together a single cavity extending through said stack;

(B) a second plurality of unapertured planar sheets of substantially porous material disposed to one side of said stack and aligned therewith;

(C) a third plurality of unapertured planar sheets of substantially porous material disposed to an opposed side of said stack and aligned therewith, said second and third pluralities of unapertured sheets extending across salad stack cavity at either end thereof to close the same and define a chamber about said cavity configured and dimensioned to receive a biological indicator, said first, second and third pluralities together defining a sheet pad;

(D) a tray formed of unapertured gas-inhibiting material, said tray having a base coextensive and aligned with the exposed side of said third plurality and four sidewalls transverse to said base together substantially covering the exposed edges of said pad, said tray and said pad together defining an assembly; and (E) an organizer disposed all about the periphery of said assembly to maintain said sheets and said tray in a predetermined spatial relationship while permitting the passage of steam and air to and from said assembly.

2. In combination, the test pack of claim 1 and a biological indicator disposed in said chamber.

3. The test pack of claim 1 wherein said sheets of said pad are of identical peripheral dimensions.

4. The test pack of claim 3 wherein said sheets of said pad are about 5×5 to 5×5.5 inch sheets.

5. The test pack of claim 1 wherein said chamber is about 1⅜×½ to 2⅝×e,fra 3/4 inch in area.

6. The test pack of claim 5 wherein said sheets of said pad are about 5×5 in. sheets, and said chamber is 1⅞× e,fra 1/2 inch in area.

7. The test pack of claim 5 wherein said sheets of said pad are about 5×5.5 in sheets, and said chamber is 2 e,fra 5/8× ×⅜ inch in area.

8. The test pack of claim 1 wherein said organizer is a box having an integrally hinged flap on one end moveable between an open position enabling passage thereinto and therefrom of said assembly and a closed position maintaining the elements of an assembly therein in a predetermined spatial disposition, said box with said flap in said closed position having an effective porosity greater than that of said pad.

9. The test pack of claim 8 wherein said first, second and third pluralities are comprised of about 14–18, 12–16 and 4–8 sheets, respectively, of paper having a basis weight of about 214 lbs., a caliper of about 0.02 in., and a Gurley porosity of about 12–35 sec. (20 oz. cylinder).

10. The test pack of claim 9 wherein said first, second and third pluralities are comprised of about 16, 14 and 6 sheets of said paper, respectively.

11. The test pack of claim 8 wherein said sheets of substantially porous material for said first, second and third pluralities are of the same composition.

12. The test pack of claim 8 wherein said box is formed of solid bleached sulphate paperboard.

13. The test pack of claim 12 wherein said paperboard has a caliper of about 0.02 inch.

14. The test pack of claim 8 wherein said box has pye locks at the corners thereof.

15. The test pack of claim 1 wherein said organizer is an overwrap sheet of paper having a substantial porosity greater than that of said pad.

16. The test pack of claim 15 wherein said first plurality is comprised of about 15–21 sheets of paper having a basis weight of about 178 lbs., a caliper of about 0.02 in., and a Frazier porosity of about 1.2–2.0 cu.ft./sq.ft./min. per sheet, and said second and third pluralities are comprised of about 17–23 and 4–8 sheets, respectively, of paper having a basis weight of about 214 lbs., a caliper of about 0.02 in., and a Gurley porosity of about 12–35 sec. (20 oz. cylinder).

17. The test pack of claim 16 wherein said first, second and third pluralities are comprised of about 18, 20 and 6 sheets of said paper, respectively.

18. The test pack of claim 15 wherein said sheets of substantially porous material for said second and third pluralities are of the same composition, and said sheets of substantially porous material for said first plurality are of a different composition.

19. The test pack of claim 15 wherein said overwrap sheet is a creped non-woven sterilization wrap sheet.

20. The test pack of claim 15 wherein said overwrap sheet is disposed in a hospital pack format about said assembly.

21. The test pack of claim 1 wherein said tray is a paperboard laminated with gas-inhibiting material.

22. The test pack of claim 21 wherein said tray is paperboard laminated on at least one side with gas-inhibiting plastic.

23. The test pack of claim 22 wherein said paperboard is solid bleached sulphate board.

24. The test pack of claim 23 wherein said plastic is polypropylene film.

25. The test pack of claim 21 wherein said tray is solid bleached sulphate having a caliper of 0.020 fully laminated on one side by acrylic adhesive with a biaxially oriented polypropylene film 0.0014 inch thick.

26. The test pack of claim 1 wherein said base and each of said sidewalls of said tray are substantially planar.

27. The test pack of claim 26 wherein said sidewalls do not overlap each other.

28. The test pack of claim 26 wherein said sidewalls overlap each other.

29. The test pack of claim 1 wherein said substantially porous material is paper.

30. A sterilization biological test pack for holding a biological indicator, the pack being suitable for use on its base in a gravity displacement steam sterilizer comprising:

(A) a first plurality of apertured planar sheets of substantially porous paper disposed to form a stack, each of said sheets defining only a generally centrally disposed aperture, and said apertures of said sheets operatively defining together a single cavity extending through said stack;

(B) a second plurality of unapertured planar sheets of substantially porous paper disposed to one side of said stack and aligned therewith;

(C) a third plurality of unapertured planar sheets of substantially porous paper disposed to an opposed side of said stack and aligned therewith, said second and third pluralities of unapertured sheets extending across said stack cavity at either end thereof to close the same and define a chamber about said cavity configured and dimensioned to receive a biological indicator, said first, second and third pluralities together defining a sheet pad, said sheets of said pad being of identical peripheral dimensions;

(D) a tray formed of paperboard laminated on at least one side with plastic to constitute an unapertured gas-inhibiting material, said tray having a base coextensive and aligned with the exposed side of said third plurality and four sidewalls transverse to said base together substantially covering the exposed edges of said pad, said tray and said pad together defining an assembly;

(E) an organizer disposed all about the periphery of said assembly to maintain said sheets and said tray in a predetermined spatial relationship while permitting the passage of steam and air to and from said assembly; and (F) a biological indicator disposed in said chamber.

31. The test pack of claim 30 wherein said organizer is a box having an integrally hinged flap on one end movable between an open position enabling passage thereinto and therefrom of said assembly and a closed position maintaining the elements of an assembly therein in a predetermined spatial disposition, said box with said flap in said closed position having an effective porosity greater than that of said pad; and said first, second and third pluralities are comprised of about 14–18, 12–16 and 4–8 sheets, respectively, of paper having a basis weight of about 214 lbs., a caliper of about 0.02 in., and a Gurley porosity of about 12–35 sec. (20 oz. cylinder).

32. The test pack of claim 30 wherein said organizer is an overwrap sheet of paper having a substantial porosity greater than that of said pad, said overwrap sheet having a basis weight of about 43 lbs. and being disposed in a hospital pack format about said assembly and said first plurality is comprised of about 15–21 sheets of paper having a basis weight of about 178 lbs., a caliper of about 0.02 in., and a Frazier porosity of about 1.2–2.0 cu.ft./sq. ft./min. per sheet, and said second and third pluralities are comprised of about 17–23 and 4–8 sheets, respectively, of paper having a basis weight of about 214 lbs., a caliper of about 0.02 in., and a Gurley porosity of about 12–35 sec. (20 oz. cylinder).

33. A customizable sterilization biological test pack for holding a biological indicator, comprising:

(A) a first plurality of apertured planar sheets of substantially porous material disposed to form a stack, each of said sheets defining only a generally centrally disposed aperture, and said apertures of said sheets operatively defining together a single cavity extending through said stack;
(B) a second plurality of unapertured planar sheets of substantially porous material disposed to one side of said stack and aligned therewith;
(C) a third plurality of unapertured planar sheets of substantially porous material disposed to an opposed side of said stack and aligned therewith, said second and third pluralities of unapertured sheets extending across said stack cavity at either end thereof to close the same and define a chamber about said cavity configured and dimensioned to receive a biological indicator, said first, second and third pluralities together defining a sheet pad;
(D) a tray formed of unapertured gas-inhibiting material, said tray having a base coextensive and aligned with the exposed side of said third plurality and four sidewalls transverse to said base together substantially covering the exposed edges of said pad, said tray and said pad together defining an assembly; and
(E) a removable organizer disposed all about the periphery of said assembly to maintain said sheets and said tray in a predetermined spatial relationship while permitting the passage of steam and air to and from said assembly;
said second and third pluralities being unequal and codependently variable for customization of the pack so long as the total of said second and third pluralities remains a constant.

34. A method of customizing a sterilization biological test pack for holding a biological indicator; the test pack comprising:
(A) a first plurality of apertured planar sheets of substantially porous material disposed to form a stack, each of the sheets defining only a generally centrally disposed aperture, and the apertures of the sheets operatively defining together a single cavity extending through the stack;
(B) a second plurality of unapertured planar sheets of substantially porous material disposed to one side of the stack and aligned therewith;
(C) a third plurality of unapertured planar sheets of substantially porous material disposed to an opposed side of the stack and aligned therewith, the second and third pluralities of unapertured sheets extending across the stack cavity at either end thereof to close the same and define a chamber about the cavity configured and dimensioned to receive a biological indicator, the first, second and third pluralities together defining a sheet pad;
(D) a tray formed of unapertured gas-inhibiting material, the tray having a base coextensive and aligned with the exposed side of the third plurality and four sidewalls transverse to the base together substantially covering the exposed edges of the pad, the tray and the pad together defining an assembly; and
(E) a removable organizer disposed all about the periphery of the assembly to maintain the sheets and the tray in a predetermined spatial relationship while permitting the passage of steam and air to and from the assembly;
said method comprising the step of codependently varying the second and third pluralities while maintaining the total of the second and third pluralities a constant.

35. The method of claim 34 wherein the second and third pluralities are codependently varied by removing at least one sheet from one of the second and third pluralities and adding the removed at least one sheet to the other of the second and third pluralities.

36. The method of claim 34 additionally including the initial step of removing the organizer from the assembly and the final step of re-disposing the organizer about the assembly.

* * * * *